(12) United States Patent
Vigil

(10) Patent No.: US 10,362,816 B1
(45) Date of Patent: Jul. 30, 2019

(54) EXPANDABLE HEADBAND

(71) Applicant: Yvette C Vigil, Cedar Hill, TX (US)

(72) Inventor: Yvette C Vigil, Cedar Hill, TX (US)

(*) Notice: Subject to any disclaimer, the term of this patent is extended or adjusted under 35 U.S.C. 154(b) by 104 days.

(21) Appl. No.: 15/430,023

(22) Filed: Feb. 10, 2017

Related U.S. Application Data

(60) Provisional application No. 62/308,293, filed on Mar. 15, 2016.

(51) Int. Cl.
*A41D 15/00* (2006.01)
*A41D 20/00* (2006.01)
*A61F 9/04* (2006.01)

(52) U.S. Cl.
CPC ............. *A41D 15/00* (2013.01); *A41D 20/00* (2013.01); *A61F 9/045* (2013.01)

(58) Field of Classification Search
CPC .......... A42B 1/20; A42B 1/201; A41D 15/00; A41D 20/00; A61F 9/045
See application file for complete search history.

(56) References Cited

U.S. PATENT DOCUMENTS

| | | | | |
|---|---|---|---|---|
| 625,776 A * | 5/1899 | Von Klein | ............ | A42C 5/04 2/171.6 |
| 1,665,750 A * | 4/1928 | McKee | ............ | A42B 1/062 2/12 |
| 3,014,220 A * | 12/1961 | Weld | ............ | A42B 1/201 2/171 |
| 3,026,525 A * | 3/1962 | Gyorfy | ............ | A42B 3/225 2/202 |
| 3,991,422 A * | 11/1976 | Saotome | ............ | A42B 3/322 2/410 |
| 4,291,417 A * | 9/1981 | Pagano | ............ | A42B 1/201 2/202 |
| 4,675,916 A * | 6/1987 | Orsini | ............ | A42B 1/201 135/143 |
| 4,741,053 A * | 5/1988 | Okamura, Sr. | ............ | A42B 1/22 2/12 |
| D738,596 S * | 9/2015 | Tang | ............ | D2/876 |
| D756,612 S * | 5/2016 | Broderick | ............ | D2/880 |
| 9,861,149 B1 * | 1/2018 | Strollo | ............ | A42B 1/006 |
| 2005/0279396 A1 * | 12/2005 | Choi | ............ | A45B 11/04 135/133 |
| 2011/0083251 A1 * | 4/2011 | Mandell | ............ | A42B 1/068 2/209 |

FOREIGN PATENT DOCUMENTS

| | | | | |
|---|---|---|---|---|
| DE | 879170 C | * | 6/1953 | ............ A42B 1/201 |
| FR | 772253 A | * | 10/1934 | ............ A42B 1/201 |
| FR | 1107381 A | * | 12/1955 | ............ A42B 1/201 |
| GB | 772288 A | * | 4/1957 | ............ A42B 1/045 |

* cited by examiner

*Primary Examiner* — Shaun R Hurley
*Assistant Examiner* — Andrew Wayne Sutton
(74) *Attorney, Agent, or Firm* — Kenneth L. Tolar

(57) ABSTRACT

An expandable headband includes an elongated, pleated-fabric cover having two opposing ends, a front edge and a rear edge. The two opposing ends are interconnected with an elastomeric strap for securing the cover over the head as with a conventional headband. To form a sun visor, a wearer pulls an extendable support rod at the front edge to expand the cover beyond the forehead.

6 Claims, 2 Drawing Sheets

EXPANDABLE HEADBAND

CROSS REFERENCE TO RELATED APPLICATIONS

This application is entitled to the benefit of provisional patent application No. 62/308,293 filed on Mar. 15, 2016, the specification of which is incorporated herein by reference.

BACKGROUND OF THE INVENTION

The present invention relates to a headband that can be conveniently expanded to form a sun visor.

DESCRIPTION OF THE PRIOR ART

Many people wear a headband as a decoration or to keep hair out of one's face and eyes. However, in order to shield the face and eyes from direct sunlight, a wearer must replace the headband with a hat or a towel. Separately transporting and wearing multiple head coverings is burdensome, inconvenient and irritating.

Accordingly, there is currently a need for a headband that can effectively block sunlight. The present invention addresses this need by providing a pleated headband with integral support rods that allow the headband to expand beyond a wearer's forehead to form a sun visor.

SUMMARY OF THE INVENTION

The present invention relates to an expandable headband comprising an elongated, pleated-fabric cover having two opposing ends, a front edge and a rear edge. The two opposing ends are interconnected with an elastomeric strap for securing the cover over the head as with a conventional headband. To form a sun visor, a wearer pulls an extendable support rod at the front edge of the cover to expand the headband beyond the forehead to form a visor.

It is therefore an object of the present invention to provide a headband that can be quickly and easily expanded to form a sun visor.

It is therefore another object of the present invention to provide an expandable headband that eliminates the burdensome task of transporting and wearing two or more head coverings while outdoors.

Other objects, features, and advantages of the present invention will become readily apparent from the following detailed description of the preferred embodiment when considered with the attached drawings and the appended claims.

DESCRIPTION OF THE PREFERRED EMBODIMENT

Figure 5:
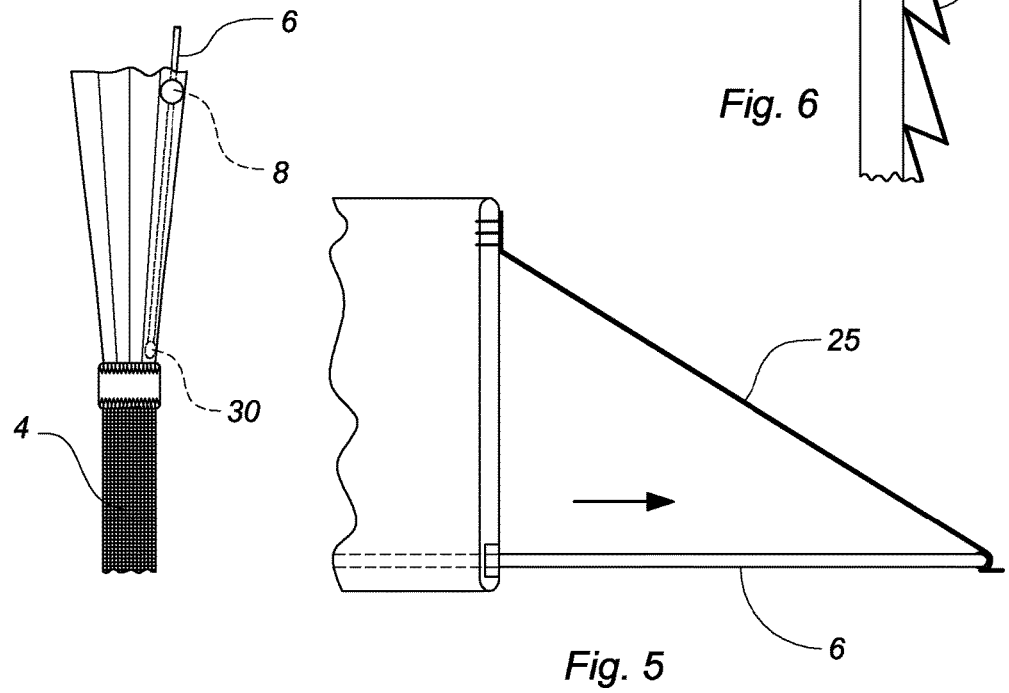
FIG. 5 is the sectional view of the headband as depicted in FIG. 4 with the upper layer expanded to form a visor.

The present invention relates to an expandable headband comprising an elongated cover 1 having two opposing ends, a front edge 2 and a rear edge 3. The cover is formed of a pleated-fabric upper layer 25 attached to a fabric lower layer 26. The upper layer is attached to the lower layer with elastomeric, triple stitching 27 for enhanced strength. The stitching 27 pulls the upper layer into the pleated orientation in the absence of tension, while allowing it to assume a substantially planar orientation when pulled into an expanded orientation, as depicted in FIG. 5.

The two opposing ends of the cover are interconnected with an elastomeric strap 4 for firmly securing the cover over the head as with a conventional headband. The front edge of the cover upper layer includes an elongated channel 5 extending from one end to the opposing end. Received within the channel is an elongated, flexible but rigid support rod 6 that conforms to a wearer's head when the headband is collapsed but sturdily supports the headband when expanded to form a visor. The support rod is formed of two sections that are joined with a ferromagnetic ferrule 7 that is attached to a central portion of the cover upper layer 25.

A pair of buttons 8 attached to the upper layer 25 each include a central passageway that is aligned with the channel. Each rod section is slidably received within one of the button passageways to allow the rod to deploy and retract concomitant with the upper layer. The rod sections are frictionally received within the passageways so that the pleated upper layer remains at a select position when released. A nodule 30 at a distal end of each section prevents the rod from being ejected from the button when the cover is being expanded. A magnet 11 on a central portion of the lower layer 26 adheres to the ferrule 7 to maintain the cover in the collapsed configuration when the rods are retracted.

Figure 1:
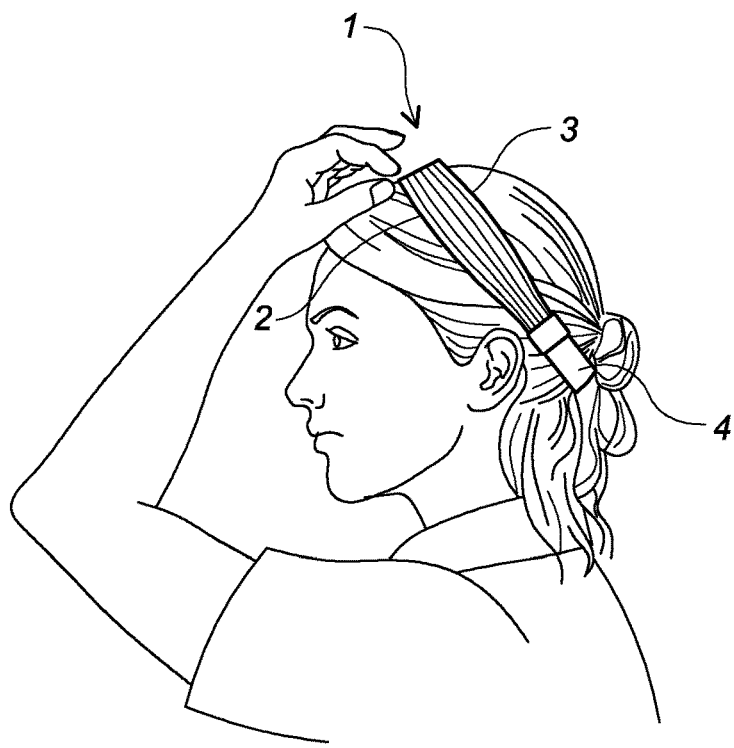
FIG. 1 depicts the headband according to the present invention present invention being worn in a collapsed orientation.
Figure 2:
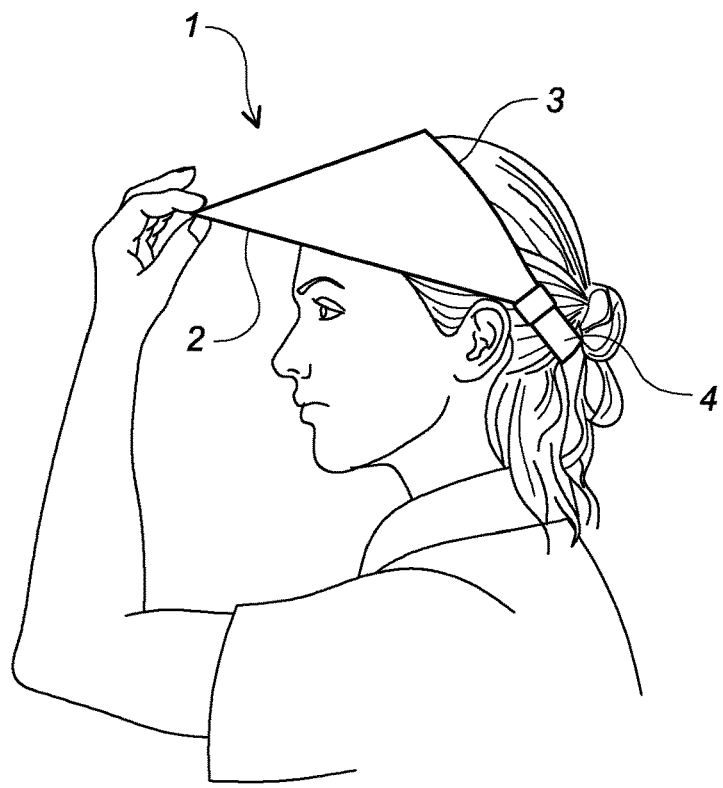
FIG. 2 depicts the headband of FIG. 1 expanded to form a visor.
Figure 3:
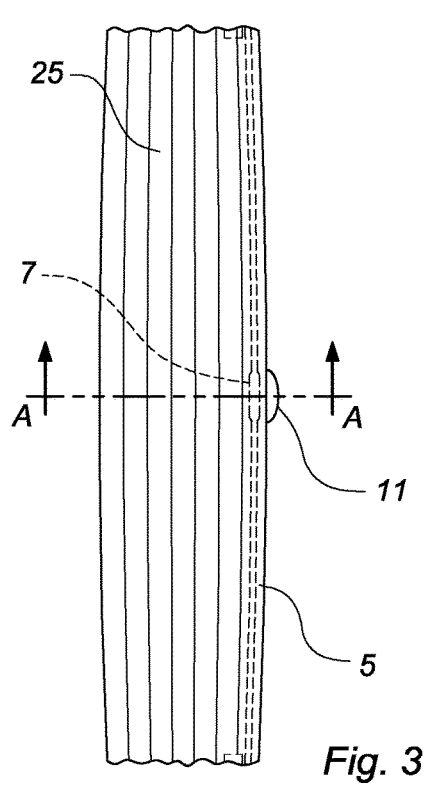
FIG. 3 is a plan, cutaway view of the expandable headband.
Figure 4:
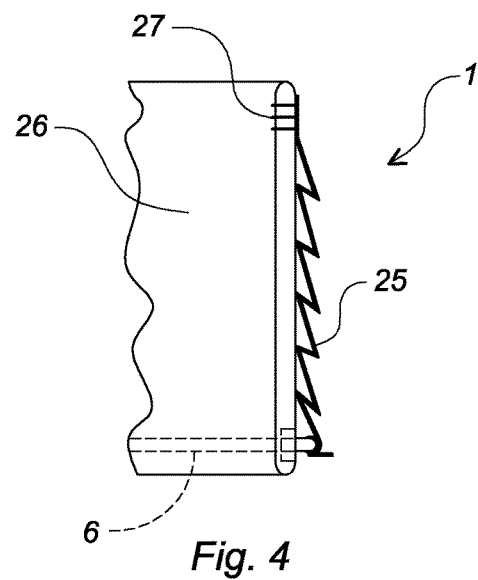
FIG. 4 is a sectional view of the headband taken along A-A of FIG. 3 with a portion of the cover perpendicularly oriented relative to a remaining portion, and with the upper layer collapsed to form a conventional headband.
Figure 6:
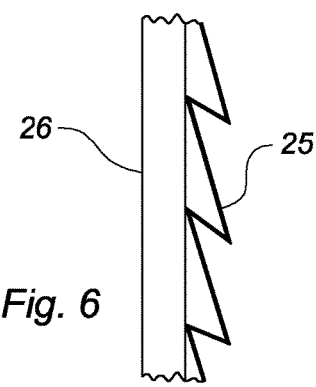
FIG. 6 is a cutaway, sectional view of the cover.

Accordingly, the device is secured over the head with the cover resting atop the crown, similarly to a conventional headband, as depicted in FIG. 1. To form a sun visor, the wearer grasps and pulls the ferrule to extend the rod and expand the cover beyond the forehead, as depicted in FIG. 2.

The above-described device is not limited to the exact details of construction and enumeration of parts provided herein. Furthermore, the size, shape and materials of construction of the various components can be varied without departing from the spirit of the present invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:
1. An expandable headband comprising:
an elongated, pleated, expandible cover having two opposing ends, a front edge and a rear edge;
means for securing the cover whereby the cover is adapted to rest atop a wearer's crown to form a headband;
an extendable support rod integral with the front edge of the cover that allows a wearer to grasp the front edge and expand the cover to form a visor;
an elongated channel on the front edge of said cover, said channel receiving said support rod;

a pair of buttons attached to said cover, each of said buttons having a central passageway aligned with said channel, a portion of said rod slidably received within each of said passageways to allow the rod to deploy and retract concomitant with expansion of the cover.

2. The expandable headband according to claim 1 wherein said rod is frictionally received within the passageway to maintain a select position when released.

3. The expandable headband according to claim 1 further comprising a nodule at each of two ends of said rod to retain said rod within the buttons when the cover is being deployed.

4. The expandable headband according to claim 1 wherein said means for securing the cover comprises an elastomeric strap interconnecting the two opposing ends.

5. The expandable headband according to claim 1 wherein said cover comprises a pleated upper layer attached to a lower layer, said upper layer having said support rod attached thereto.

6. The expandable headband according to claim 5 further comprising:
- a magnet on said lower layer;
- a ferromagnetic ferrule on said support rod for adhering to said magnet when the cover is collapsed to form a headband.

* * * * *